United States Patent [19]

Wolfe

[11] 4,030,142
[45] June 21, 1977

[54] OCCLUDER FOR PROSTHETIC HEART VALVE ASSEMBLY

[75] Inventor: Gerald W. Wolfe, Paradise, Calif.

[73] Assignee: InterMed, Inc., Wayne, Pa.

[22] Filed: Mar. 26, 1976

[21] Appl. No.: 670,690

[52] U.S. Cl. .................................. 3/1.5; 137/847
[51] Int. Cl.² ........................................ A61F 1/22
[58] Field of Search ................ 3/1.5; 137/846, 847

[56] References Cited

UNITED STATES PATENTS

| 3,308,798 | 3/1967 | Snider | 137/846 X |
|---|---|---|---|
| 3,513,485 | 5/1970 | Davila | 3/1.5 |
| 3,556,122 | 1/1971 | Laerdal | 137/846 X |
| 3,717,883 | 2/1973 | Mosher | 3/1.5 |
| 3,839,741 | 10/1974 | Haller | 3/1.5 |

FOREIGN PATENTS OR APPLICATIONS 482,441  12/1969  Switzerland ........................... 3/1.5

Primary Examiner—Ronald L. Frinks
Attorney, Agent, or Firm—Weiser, Stapler & Spivak

[57] ABSTRACT

An occluder for a prosthetic heart valve assembly adapted within a seating-ring passage having a body including a downstream sealing section comprising a plurality of cuspids which engage each other to define a closed sealing section when the occluder is in its closed position and which flex outwardly relative to each other when the occluder is in its open position to define a central open passage through the occluder, and an armature reinforcing the body. The armature includes an annular ring and a plurality of reinforcing arms hingedly connected to the ring and extending through each cuspid to permit flexure of each arm relative to the annular ring.

9 Claims, 11 Drawing Figures

OCCLUDER FOR PROSTHETIC HEART VALVE ASSEMBLY

BACKGROUND OF THE INVENTION

1. Field of the Invention

This invention relates to prosthetic heart valve assemblies, and more specifically to a unique center-flow occluder of such assemblies.

2. Description of the Prior Art

It is known in the prior art to replace a diseased defective valve in the human heart with a prosthetic, or artificial heart valve assembly. In many cases, a patient has continued to live for many years with such a prosthetic heart valve assembly.

Prosthetic heart valve assemblies which most closely approximate the action of natural heart valves are of the center-flow type. Specifically, these prosthetic heart valve assemblies include an elongate occluder which is movable between closed and opened positions within a seating-ring passage of a valve seat assembly. The occluder includes a plurality of cuspids which are movable radially which respect to each other between a closed condition when the occluder is in a closed position, and an opened condition when the occluder is in an opened position. When the cuspids are in their opened condition blood can flow through the interior thereof to simulate the action of a natural heart valve.

The center-flow occluders disclosed in prior art prosthetic heart valve assemblies preferably are formed of a plastic material, such as polypropylene, since such a material is generally lightweight and easily formable into the desired configuration for use in heart valve assemblies. It has been discovered that these center-flow occluders, and particularly the cuspids thereof, become deformed after continued usage. Deformation of the cuspids prevents the occluder from effectively sealing the opening through the valve seat assembly when the occluder is in its closed position. This ineffective sealing of the heart valve assembly causes an undesirable leakage of blood through the seating-ring passage.

SUMMARY OF THE INVENTION

This invention relates to improvements in center-flow occluders of prosthetic heart valve assemblies. The heart valve assemblies of this invention are especially designed for implantation in the human heart to replace the natural mitral valve; however, the valve assemblies of this invention also can be adapted to replace the tricuspid and/or aortic valves.

An elongate occluder of this invention is adapted to be positioned through a seating-ring passage for movement in its direction of elongation between closed and opened positions. The occluder includes an upstream annular section and a downstream sealing section, both of which have a maximum diameter that is larger than the minimum diameter of the seating-ring passage. This dimensional relationship prevents the occluder from moving out of the seating-ring passage. The downstream sealing section of the occluder is of a split construction provided by a plurality of cuspids. The cuspids are connected to the upstream annular section through flexible stems, and are movable radially with respect to each other between a closed condition in which they engage each other, and an opened condition in which they are radially spaced apart to provide a passage through the occluder for the flow of blood.

At least the cuspids of the occluder are formed of a plastic material, such as polypropylene, which is light in weight, and easily formable into the desired configuration.

An armature construction having greater dimensional stability than the cuspids of the occluder includes an upstream annular ring and a plurality of arms which extends downwardly from said ring in circumferentially spaced-apart relationship to each other. The upstream end of each arm is connected to the annular ring through a hinge section, and each arm extends in a downstream direction through the interior of a respective cuspid. Since each of the arms is connected through a hinge to the upstream annular ring the required flexing action of the plastic cuspids is not impaired by the reinforcing arms. Moreover, since the arms have greater dimensional stability than the plastic cuspids they will reinforce the cuspids to ensure that deformation of said cuspids does not take place. The unique cooperation between the reinforcing arms and cuspids, as described above, represents a considerable improvement over prosthetic heart valve assemblies employing center-flow occluders, and is neither shown nor suggested by any of the prior art that applicant is aware of.

In one embodiment of this invention the upstream annular section, flexible stems and cuspids of the occluder are molded about the armature construction as a unitary plastic body. In this embodiment the annular ring of the armature construction is disposed within the interior of the upstream annular section of the plastic body, and the downwardly extending arms of the armature construction are disposed within the interior of the flexible stem and cuspids of the plastic body.

In an altenative embodiment of this invention the plastic cuspids are molded individually, and the armature construction is formed as a unitary member. In this embodiment the arms of the armature construction are disposed within the interior of respective cuspids to properly position the cuspids relative to each other. The upstream annular section and flexible stems of the occluder are provided by sections of the unitary armature construction.

It is an object of this invention to provide a center-flow occluder for a heart valve assembly in which a plurality of radially movable cuspids are dimensionally reinforced without impairing the required movement of the cuspids.

It is a further object of this invention to provide a center-flow occluder for a heart valve assembly which promotes unrestricted, streamlined, hydraulic flow of blood through the interior thereof in a manner simulating the action of a natural heart valve.

Other objects and a fuller understanding of the invention will become apparent by referring to the following description, taken in conjunction with the drawings.

DESCRIPTION OF THE PREFERRED EMBODIMENTS OF THE INVENTION

The center-flow occluders of this invention preferably are employed in prosthetic heart valve assemblies adapted to replace the natural mitral valve in the human heart. The prosthetic mitral valve is inserted between the left atrium and left ventricle of the heart. Blood flows into the left atrium from the lungs through the pulmonary veins, and then through the prosthetic mitral heart valve assembly into the left ventricle from where it is pumped through the aortic valve for distribution through the body. When the ventricle contracts to pump the blood through the aortic valve, the resulting pressure should close the heart valve assembly to prevent the reverse flow of blood back into the atrium. Upon relaxation, or expansion of the ventricle, the pressure built up by blood entering the atrium through the pulmonary veins should open the heart valve assembly to permit blood to flow from the atrium into the ventricle. The above-described sequence is repeated continuously during normal operation of the heart.

Figure 1:
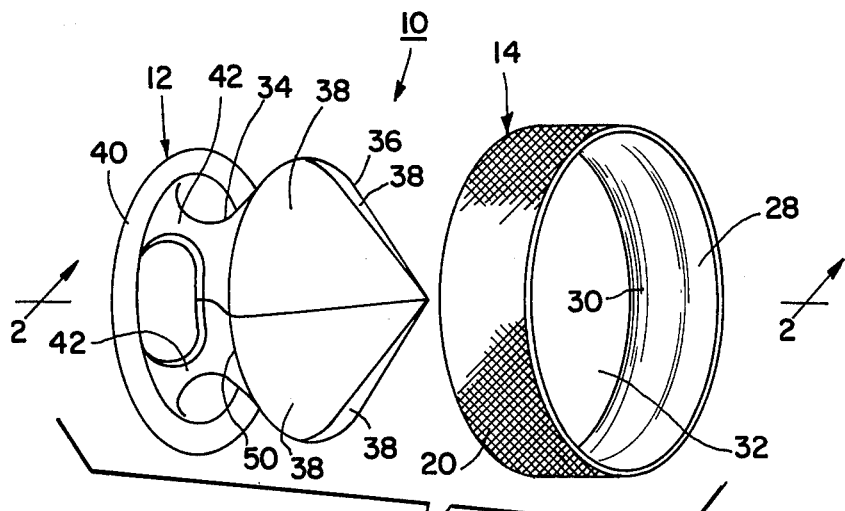
FIG. 1 is an exploded isometric view of a prosthetic heart valve assembly employing a unique occluder in accordance with this invention.

Referring to FIG. 1, a prosthetic mitral heart valve assembly 10 includes a unique center-flow occluder 12 disposed for movement within a valve seat assembly 14. The valve seat assembly 14, in accordance with the broadest aspects of this invention, can be of any suitable construction which provides a passageway in which the occluder 12 is movable.

Figures 2A, 2B:
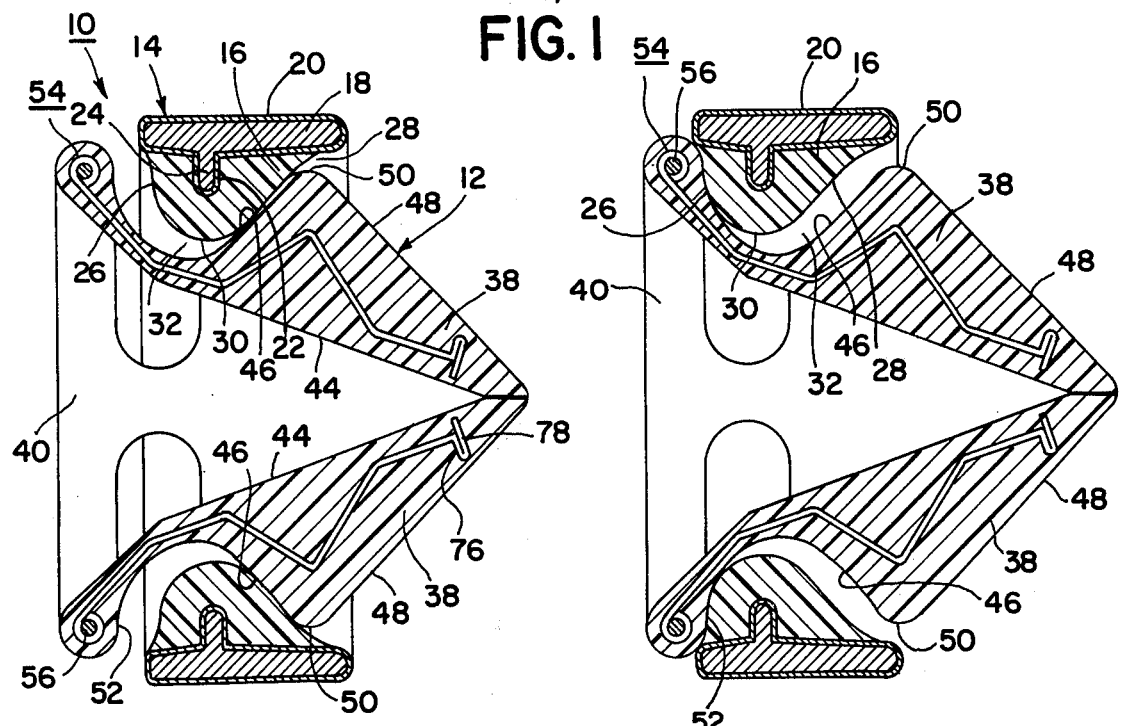
FIG. 2A is a sectional view taken along line 2—2 of the heart valve assembly shown in FIG. 1 with the elements assembled and disposed in a valve-closing position.
FIG. 2B is a sectional view similar to FIG. 2A, but showing the valve assembly in an opened position.

Referring to FIG. 2A, a preferred valve seat assembly 14 includes a soft seating ring 16, a hard, rigid, cast supporting ring 18 and a fixation cover 20. The seating ring 16 preferably is made of silicone, or other equivalent material, and is molded with a recess 22 disposed continuously about its outer periphery. The supporting ring 18 can be formed of a hard plastic or metallic material, and includes an inwardly directed annular projection 24 which is disposed within the recess 22 of the seating ring 16 to maintain the seating ring in its desired configuration. The fixation cover 20, which is a Dacron mesh cloth or other suitable material, is secured about the supporting ring 18, and is initially secured to the heart tissue by suturing. After the fixation cover 20 has been sutured to the heart tissue, thrombosis, which is the formation of clots, is relied upon to retain the valve seat assembly 14 in its proper position within the heart.

Figure 2C:
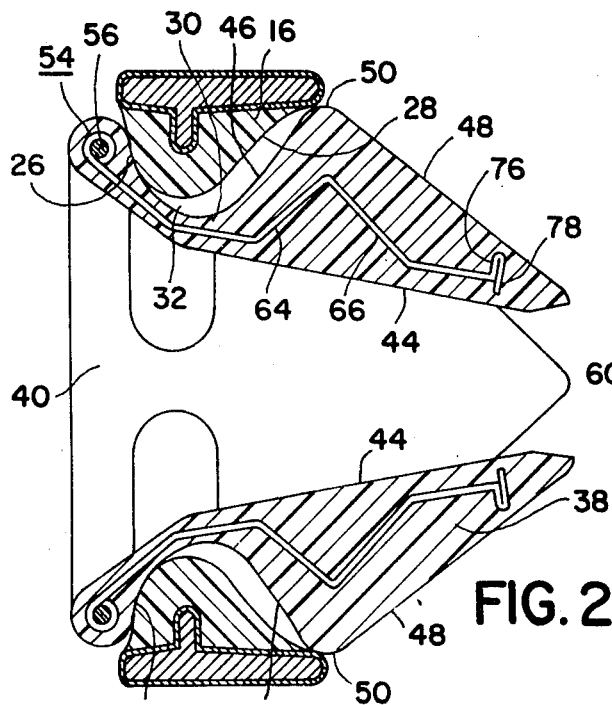
FIG. 2C is a sectional view similar to FIG. 2B, but with the valve assembly in a different condition in its opened position.

Referring to FIGS. 2A-2C, the seating ring 16 has an outwardly flared section 26 facing in an upstream direction, and an outwardly flared section 28 facing in a downstream direction. The flared sections 26 and 28 are connected at a junction 30 which establishes the minimum diameter of a passageway 32 through the seating ring 16.

Referring again to FIG. 1, the center-flow occluder 12, in accordance with one embodiment of this invention, includes a one-piece plastic body 34 of a suitable synthetic material such as polypropylene. The occluder 12 includes a downstream sealing section 36 of a split construction providing a plurality of cuspids 38. The occluder 12 shown in FIG. 1 has four cuspids 38; however, the number of cuspids can be varied as desired. The more practical designs include from two to four cuspids. Each of the cuspids 38 is joined to an upstream annular section 40 through a stem section 42.

Each of the cuspids 38 includes a substantially smooth inner surface 44 which is free of sharp angles or bends to aid in providing a streamlined flow path for blood when said cuspids are in an open condition as shown in FIG. 2C. Each cuspid 38 also includes an outer surface which is defined by upstream and downstream flared sections 46 and 48, respectively. These flared sections are joined through a rounded apex 50 which, when the cuspids 38 are in a closed condition as shown in FIGS. 2A and 2B, define a continuous circle of a greater diameter than the circle defined by junction 30 of the seating ring 16 (FIG. 1). Accordingly, the occluder 12 cannot move out of the seating ring in an upstream direction. Moreover, the upstream flared sections 46, when the cuspids 38 are in a closed condition, define a continuous annular surface which is substantially complimentary to the outwardly flared section 28 of the seating ring 16. Accordingly, in the closed position of the heart valve assembly 10 as shown in FIG. 2A, the flared sections 46 of the cuspids 38 will seat on the outwardly flared section 28 of the seating ring 16 to seal off the atrium from the ventricle as the ventricle contracts.

The upstream annular section 40 of the occluder 12 has an outwardly flared surface 52 which overlies the outwardly flared section 26 of the seating ring 16. The flared surface 52 is substantially complimentary in shape to the flared section 26. Accordingly, the upstream annular section 40 of the occluder seats on the flared section 26 of the seating ring 16 when the occluder 12 is in its opened position (FIGS. 2B and 2C) to prevent the occluder from moving out of the seating ring passageway 32 in a downstream direction.

When the ventricle contracts the back pressure acts against the downstream flared sections 48 of the cuspids 38 to force the occluder into its valve sealing position shown in FIG. 2A. The camming action between upstream flared section 46 of each cuspid 38 and the inner surface of the seating ring 16 assists in forcing the cuspids 38 into engagement with each other to seal off the central passage through the occluder 12. When the ventricle expands, or relaxes, blood entering the atrium through the pulmonary veins will establish a pressure drop across the heart valve assembly 10 to move the occluder 12 into its opened condition shown in FIG. 2C. In this opened condition the cuspids 38 are flexed radially outwardly from each other to provide an uninterrupted flow path through the center of the occluder 12. As the highest pressure in the heart shifts from the ventricle to the atrium during operation of the heart an interval of time will exist when there is substantially a zero pressure drop across the heart valve assembly 10. The same zero pressure drop will exist when the highest pressure within the heart shifts from the atrium to the ventricle. During these periods of zero pressure drop across the heart valve assembly 10 the occluder 12 may, due to the chest position of the user, be disposed in its open position shown in FIG. 2B. However, just as is the case with a natural heart valve, the cuspids 38 will remain in a closed condition to seal off the central passage through the occluder 12.

In order for the heart valve assembly 10 to properly operate for its required life two factors are extremely important. First, the occluder must have dimensional stability so that it will properly seat against the seating ring 16 to prevent the leakage of blood from the ventricle to the atrium when the valve assembly is closed. Secondly, the cupids 38 must be capable of continuously flexing between their opened and closed conditions without malfunctioning. The improvements to center-flow occluders in accordance with this invention accomplishes both of these objectives.

Referring to FIGS. 2A-2C, 3 and 4, the occluder 12 includes a unique reinforcing armature construction 54 for establishing shape stability of the occluder 12, while still permitting the cuspids 38 to properly flex about their stem sections 42. The armature construction 54 preferably is constructed of a metallic material having greater structural stability than the material which is employed to form the occluder body 34. For example, titanium has been employed satisfactorily in the fabrication of the armature construction 54. Preferably the plastic body 34 of the occluder 12 is molded about the armature construction 54 so that armature construction is disposed within the interior of the plastic body.

The armature construction 54 includes a continuous annular ring 56 disposed within the upstream annular section 40 of the occluder 12 (FIGS. 2A-C). A plurality of arms 58 are secured to the ring 56 through hinge sections 60; each arm extending in a downstream direction through the cuspids 38. The hinge connection between each arm 58 and the ring 56 is extremely important, and is necessary in order to permit flexing of the cuspids to take place without the possiblity of binding.

Referring to FIGS. 2A-2C, the cuspids 38 preferably are constructed with their thickest region in transverse alignment with the rounded apex 50. In order to properly reinforce that region so that the outer configuration of each cuspid does not becomes distorted during use, each arm 58 includes transversely offset, inclined sections 64 and 66 disposed at an angle of approximately 90° to each other. These inclined sections provide sufficient reinforcement for the cuspids 38 in their thickest region to prevent the outer configuration of said cuspids from becoming distorted during use. As explained earlier, distortion of the outer configuration of the cuspids 38 will prevent proper conformation of the occluder 12 with the seating ring 16; resulting in undesirable leakage of blood from the ventricle into the atrium when the valve assembly 10 is closed.

Figure 3:
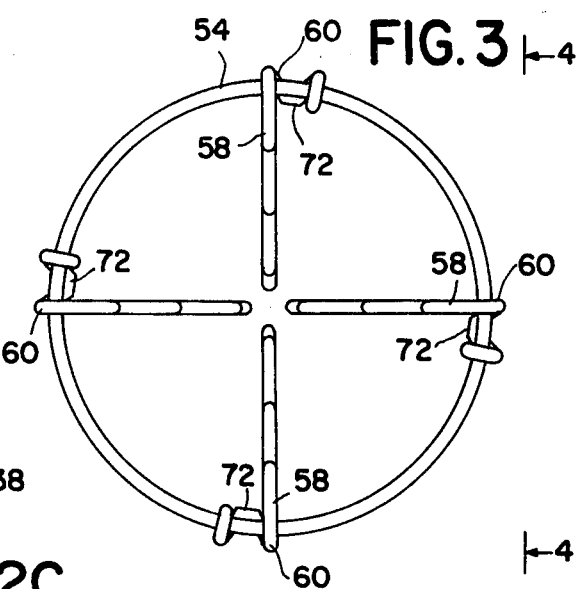
FIG. 3 is a rear view of an armature construction employed in the occluder shown in FIG. 1.
Figure 4:
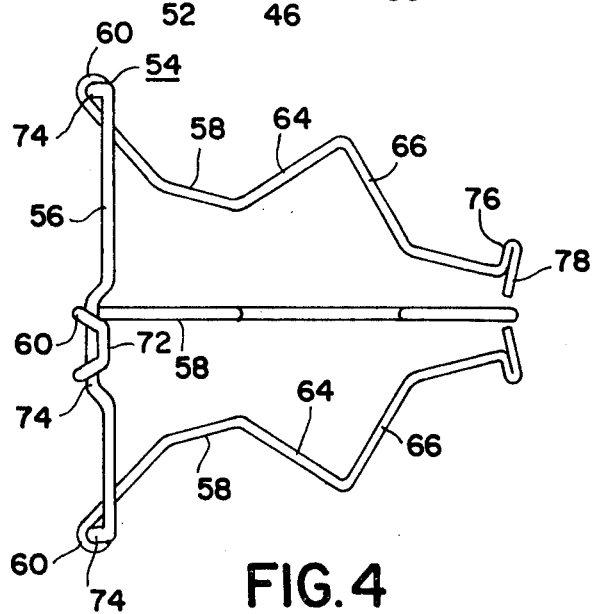
FIG. 4 is a side elevation view of the armature construction taken along line 4—4 of FIG. 3.
Figure 5:
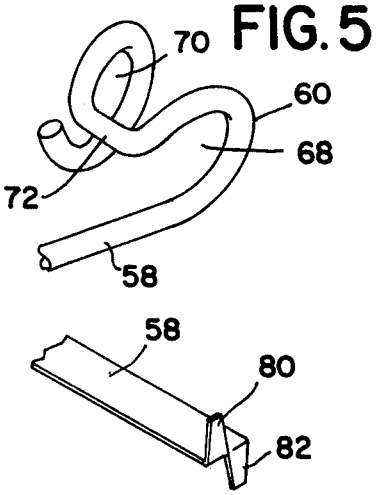
FIG. 5 is an enlarged isometric view of the upstream hinge end of an arm employed in the armature construction.

Referring to FIGS. 3-5, the hinge section 60 of each arm 58 is formed by a bent upstream end of the arm to form transversely aligned passages 68 and 70 connected to each other through a clip section 72. The clip section 72 can be forced outwardly over the annular ring 56 to provide a snap-friction fit with said ring while still permitting adequate hinging action between the ring 56 and the arms 58.

Referring to FIG. 4, the annular ring 56 includes hinge-locating offsets 74 which are spaced 90° apart. These hinge-locating offsets receive the hinge section 60 of respective arms 58 to prevent the arms from moving circumferentially about the annular ring. The number of hinge-locating offsets 74 will depend upon the number of cuspids employed in the occluder 12. For example, if only two cuspids are employed in the occluder, only two hinge-locating offset 74 will be provided, and these offsets will be disposed 180° from each other.

Referring to FIGS. 2A-2C and 4, the downstream end of each arm 58 is provided with overlapping bent sections 76 and 78. These bent sections are employed to properly position the arms 58 within a mold as plastic body 34 of the occluder is molded about the armature construction. Moreover, these bent sections, by virtue of extending transversely of the general downstream direction of the arms 58, provide additional reinforcement for the downstream end of the cuspids 38.

Figure 6:
FIG. 6 is a partial isometric view showing a modified construction of the downstream end of the arms employed in the armature construction.

Referring to FIG. 6, an alternative construction is shown for the downstream end of each arm 58. Specifically each arm 58 is split and bent to provide oppositely directed tabs 80 and 82, respectively. These tabs provide the same function as the overlapping bent sections 76 and 78 described in the preceding paragraph.

Figures 8, 9:
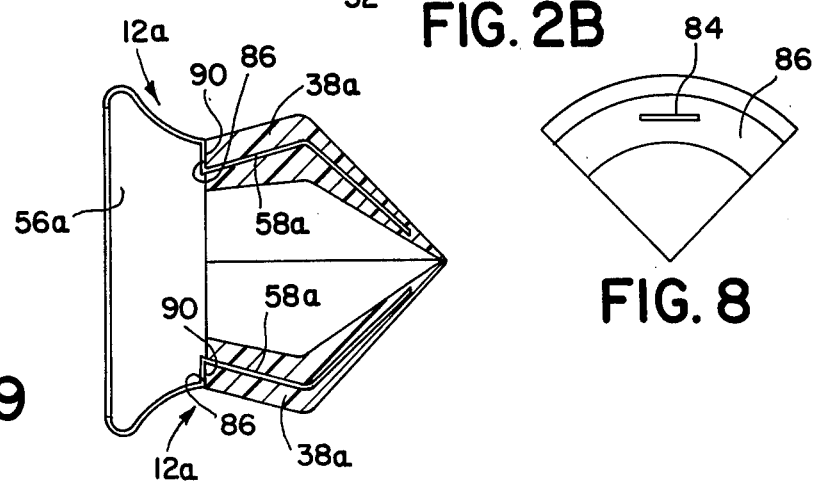
FIG. 8 is a plan view of a cuspid taken along line 8—8 of FIG. 7.
FIG. 9 is a sectional view taken along line 9—9 of FIG. 7 with the elements of the occluder assembled.
Figure 7:
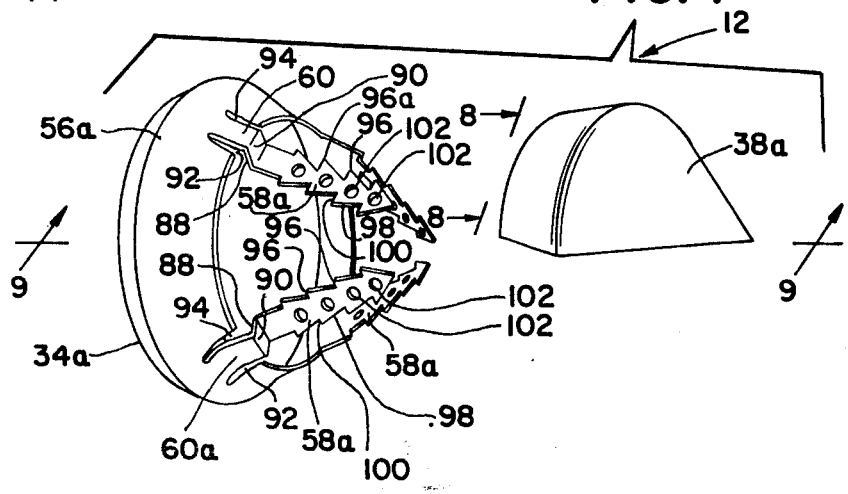
FIG. 7 is an exploded isometric view of a second embodiment of an occluder according to this invention with only one cuspid shown for purpose of clarity.

Referring to FIGS. 7-9, a second embodiment of a center-flow occluder 12a includes separately molded, unitary cuspids 38a. Only one cuspid 38a is shown in FIG. 7 for purpose of clarity. A passage 84 is provided through each cuspid 38a, and extends in a general downstream direction from an upper surface 86 (FIGS. 8 and 9). The cuspids 38a can be formed of the same plastic material as is employed to form the one-piece plastic body 34 of the occluder 12.

Referring to FIG. 7, a unitary metallic armature construction 34a, which has greater structural rigidity than the plastic cuspids 38a, includes an upstream annular section 56a and a plurality of circumferentially spaced reinforcing arms 58a. Each of the arms 58a is connected to the annular section 56a through a hinge section 60a and a radially offset section 88. Each radially offset section 88 provides a downwardly directed shoulder 90 having a function which will be described later.

Each hinge section 60a is provided, in part, by circumferentially spaced, upwardly directed recesses 92 and 94 in the upstream annular section 56a. These upwardly directed recesses enhance the spring action of the hinge section 60a to enhance radial flexure of the arms 58a relative to each other.

Referring to FIG. 7, each of the reinforcing arms 58a includes notched side margins which provide a plurality of barbs 96. Each barb is provided by a side surface segment 98 which extends in an inclined direction toward the central axis of the arm in a downstream direction, and an upper, transversely extending surface segment 100. A plurality of cut out regions, or apertures 102 are provided along the longitudinal extending axis of each of the arms 58a to lighten the weight of each arm without adversely affecting its reinforcing capability.

In use each of the arms 58a is forced through the passage 84 in a respective cuspid 38a to properly retain the cuspids in operative position relative to each other.

The inclined surface segments 98 of the side margins of each arm 58a permits easy insertion of the arms into the passages 84 of respective cuspids 38a. The arms 58a are sufficiently flexible to follow the configuration of passages 84 (FIG. 9). The barbed construction of the side margins of each arm 58a functions in a manner similar to a fish hook, and resists the withdrawal of the arms from the cuspids. The arms 58a are inserted into the passages 84 of the cuspids 38a until the downwardly directed shoulder 90 adjacent the upstream end of each arm 58a engages the upper surface 86 of its respective cuspid (FIG. 9). In this manner the downwardly directed shoulder 90 functions to properly position each of the cuspids relative to each other.

In the embodiment shown in FIGS. 7–9, the upstream annular section of the occluder 12a is provided by the upstream annular section 56a of the armature construction, and the stem section of the occluder 12a is provided by the hinge section 60a of the armature construction.

Having described my invention, I claim:

1. An elongate occluder of a prosthetic heart valve assembly, said occluder being adapted to be positioned through a seating-ring passage for movement in its direction of elongation between closed and opened positions, said occluder including a unitary plastic body having an upstream annular section and a downstream sealing section, both of which have a larger maximum diameter than the minimum diameter of the seating-ring passage, said upstream annular section being adapted to engage a surface defining the seating-ring passage when the occluder is in an opened position and the downstream sealing section being adapted to engage a surface defining the seating-ring passage when the occluder is in its closed position, said downstream sealing section being provided by a plurality of cuspids which engage each other to define a closed sealing section when the occluder is in a closed position, a flexible stem section interconnecting the upstream annular section of the unitary plastic body with each of the cuspids for permitting outward flexure of said cuspids when the occluder is in an opened position to define a central open passage through the occluder for the flow of blood; the improvement comprising an armature construction disposed within the unitary plastic body for reinforcing said body, said armature construction including an annular ring disposed within the upstream annular section of the plastic body, and a reinforcing arm extending in a downstream direction through each flexible stem and its associated cuspid, each reinforcing arm including a hinge section adjacent its upstream end end and connected to the annular ring to permit flexure of each arm relative to said annular ring.

2. The elongate occluder according to claim 1, wherein the hinge section of each arm includes a bent upstream end of the arm providing transversely aligned passageways disposed in frictional engagement with the annular ring.

3. The elongate occluder according to claim 2, wherein the annular ring of the armature construction includes hinge-locating offset sections disposed circumferentially about said annular ring, the hinge section of each reinforcing arm being connected to said annular ring in an offset section thereof.

4. The elongate occluder according to claim 3, wherein the number of hinge-locating offset sections in the annular ring is equal to the number of cuspids of the downstream sealing section of the occluder.

5. The elongate occluder according to claim 3, wherein each reinforcing arm of the armature construction has a transversely bent downstream section.

6. The elongate occluder according to claim 1, wherein each cuspid includes an upstream and a downstream flared section, said flared sections being joined at a rounded apex which constitutes the thickest region of each cuspid, the downstream reinforcing arm associated with each cuspid having an annular offset section intermediate its ends for enhancing the reinforcement of each cuspid in the region of the apex.

7. An elongate occluder of a prosthetic heart valve assembly, said occluder being adapted to be positioned through a seating-ring passage for movement in its direction of elongation between closed and opened positions, said occluder including an upstream annular section and a downstream sealing section, both of which have a larger maximum diameter than the minimum diameter of the seating-ring passage, said downstream sealing section being provided by a plurality of cuspids which engage each other to define a closed sealing section when the occluder is in a closed position, each of said cuspids being joined to the upstream annular section through a flexible hinge section for permitting outward flexure of said cuspids when the occluder is in an opened position to define a central open passage through the occluder for the flow of blood; the improvement wherein the upper annular section and hinge section of the occluder are part of a unitary armature construction, said armature construction further including a plurality of circumferentially spaced arms extending in a downstream direction relative to the upper annular section, said cuspids being separate unitary plastic members, and each arm of the unitary armature construction extending into the interior of a respective cuspid for retaining said cuspids in their proper operative position and for reinforcing said cuspids.

8. The elongate occluder according to claim 7, wherein the upstream end of each arm is connected to a respective hinge section through a radially offset section providing a downwardly facing shoulder engaging an upstream surface of its respective cuspid for achieving the proper positioning of the cuspids relative to each other.

9. The occluder according to claim 7, wherein each arm includes a plurality of outwardly directed barbs provided at each side margin thereof, said barbs firmly engaging internal surfaces of each cuspid for retaining said cuspids in proper position relative to each other.

* * * * *